(12) United States Patent
Selveo et al.

(10) Patent No.: US 10,980,956 B2
(45) Date of Patent: Apr. 20, 2021

(54) TRACHEOSTOMA VALVE

(71) Applicant: Atos Medical AB, Horby (SE)

(72) Inventors: Thomas Selveo, Horby (SE); Ronny Magnusson, Horby (SE); Marcus Alfredsson, Horby (SE)

(73) Assignee: Atos Medical AB

( * ) Notice: Subject to any disclaimer, the term of this patent is extended or adjusted under 35 U.S.C. 154(b) by 276 days.

(21) Appl. No.: 16/090,206

(22) PCT Filed: Oct. 27, 2016

(86) PCT No.: PCT/SE2016/051045
§ 371 (c)(1),
(2) Date: Sep. 28, 2018

(87) PCT Pub. No.: WO2017/171599
PCT Pub. Date: Oct. 5, 2017

(65) Prior Publication Data
US 2019/0111225 A1    Apr. 18, 2019

(30) Foreign Application Priority Data

Apr. 1, 2016 (SE) .................................. 1650431-8

(51) Int. Cl.
*A61M 16/04* (2006.01)
*A61M 16/10* (2006.01)

(52) U.S. Cl.
CPC ...... *A61M 16/0468* (2013.01); *A61M 16/047* (2013.01); *A61M 16/1045* (2013.01)

(58) Field of Classification Search
CPC ...... A61F 2/20; A61F 2/203; A61F 2002/206; A61F 2210/009; A61M 16/0468;
(Continued)

(56) References Cited

U.S. PATENT DOCUMENTS 5,738,095 A * 4/1998 Persson ............ A61F 2/20
128/201.13
6,422,235 B1 * 7/2002 Persson ............ A61M 16/0468
128/200.26
(Continued)

FOREIGN PATENT DOCUMENTS

CN     2093653 U     1/1992
CN   102227231 A   10/2011
(Continued)

OTHER PUBLICATIONS

Walsh, Ronald A. Machinists' and Metalworkers' Pocket Reference. McGraw-Hill., 2000. p. 3-67: Figure 3.3 Relationship Between Shore Durometer Scales OO, A, and D for Elastomers. (Year: 2000).*

(Continued)

*Primary Examiner* — Annette Dixon
(74) *Attorney, Agent, or Firm* — Fishman Stewart PLLC (57) ABSTRACT

A tracheostoma device for cooperation with a tracheostoma device holder superimposed on a tracheostoma of a person includes a tubular body and a container. The tubular body is at the proximal end of the tracheostoma device. The tubular body includes at least one inlet upon exhalation through the tracheostoma device, and is adapted for cooperation with the tracheostoma device holder. The container being at the distal end of the tracheostoma device, includes at least one outlet upon exhalation through the tracheostoma device and is adapted for housing a heat and moisture exchanging foam. The tubular body and the container have a hardness of 100 Shore A or less.

18 Claims, 6 Drawing Sheets

(58) Field of Classification Search
CPC ............ A61M 16/047; A61M 16/1045; A61M 16/208; Y10S 128/26; Y10S 128/911; Y10S 128/912
See application file for complete search history.

(56) References Cited

U.S. PATENT DOCUMENTS

| | | | |
|---|---|---|---|
| 7,025,784 | B1 | 4/2006 | Blom et al. |
| 8,505,537 | B2 | 8/2013 | Persson |
| 8,991,394 | B2 | 3/2015 | Persson |
| 9,943,657 | B2 | 4/2018 | Persson |
| 2003/0029456 | A1* | 2/2003 | Lambert ........... A61M 16/0468 128/207.15 |
| 2016/0206422 | A1* | 7/2016 | Blom ....................... A61F 2/203 |
| 2016/0242900 | A1* | 8/2016 | Fahl .................. A61M 16/1045 |

FOREIGN PATENT DOCUMENTS

| | | |
|---|---|---|
| CN | 102427843 A | 4/2012 |
| CN | 104203323 A | 12/2014 |
| DE | 275183 | 1/1990 |
| DE | 202012003723 U1 | 5/2012 |
| FR | 2701834 A1 | 9/1994 |
| JP | 2002516144 A | 6/2002 |
| JP | 2010524614 A | 7/2010 |
| JP | 2012510303 A | 5/2012 |
| JP | 2015513936 A | 5/2015 |
| WO | 9419045 A1 | 9/1994 |
| WO | 2008090311 A2 | 7/2008 |
| WO | 13152755 A1 | 10/2013 |

OTHER PUBLICATIONS

English Abstract Translation for DE 202012003723, Retrieved May 2, 2019.
Espacenet document regarding Abstract not available for DD 275183, Retrieved Feb. 5, 2019.
International Search Report dated Jan. 23, 2017.
Chinese Search Report dated Jul. 16, 2020 related to corresponding Chinese Application No. 201680084305.2.
Chinese Office Action dated Jul. 23, 2020 related to corresponding Chinese Patent Application No. 201680084305.2.
Notice of Reasons for Rejection dated Sep. 29, 2020 related to corresponding Japanese Patent Application No. 2018-548170.

* cited by examiner

TRACHEOSTOMA VALVE

CROSS REFERENCE TO RELATED APPLICATIONS

This application claims priority to International Application PCT/SE2016/051045 filed on Oct. 27, 2016 and Swedish Application SE 1650431-8 filed on Apr. 1, 2016, all of which is hereby incorporated by reference in its entirety.

TECHNICAL FIELD

This invention pertains in general to a tracheostoma device. More particularly, the present invention pertains to a tracheostoma device to be connected to a tracheostoma device holder, said tracheostoma device holder comprising a skirt for attachment over a tracheostoma via the proximal side of the skirt, said skirt being provided with a through hole having a tubular tracheostoma device fitting extending distally from the skirt circumferentially of said through hole.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma device in form of a tracheostoma valve. In these situations, the valve can be arranged to remain open during breathing but can be closed to divert the airflow.

In this respect tracheostoma devices, such as filter devices, HME, breathing protectors, and speech valves, have been developed to enable moisturizing of inhaled air, removal of small particles and bacteriological substances in said inhaled air, and providing the person with the ability to speech by closing the air passage through the tracheostoma by manual operation.

These tracheostoma devices are held in place by a tracheostoma device holder, arranged above the tracheostoma of the person. The tracheostoma device holder is normally attached to the skin of the person by a plaster, having an adhesive surface on the side of the plaster intended to be directed towards the person in use. The tracheostoma device can be held in place in the tracheostoma device holder by frictional force, via a for example a ridge and a groove connection between the two, such as the one described in U.S. Pat. No. 7,025,784, wherein the device comprises a cylindrical sleeve, an annular flexible and resilient skirt projecting outward from an outside wall of the sleeve, said skirt being configured for attachment to the skin of a wearer around the tracheostoma. The device holder may hold a tracheostoma aid device, wherein either the tracheostoma device holder or the tracheostoma aid device includes an annular recess on the side wall thereof and the other of the two comprises an annular rib, wherein the recess and the rib ensures engagement between the two. A disadvantage with this device holder is that the tracheostoma aid device will be released once a retaining force threshold is overcome by exhaled air pressure. Also, the sealing effect between the tracheostoma device holder and the tracheostoma aid device will also be affected by the retaining force threshold, such that the risk of unwanted air leakage between the tracheostoma device holder and the tracheostoma aid device is increased, which will negatively affect the possibility to control for example air flow through a voice prosthesis in the oesophagal/tracheal wall. When removing the tracheostoma device it is then also necessary to overcome the very same frictional force, which simultaneously must ensure sealing and retention, which means that these two parameters both must be taken into account—meaning that one of them cannot be maximized since it would hamper the other. Still further, the material rigidity of the two components, i.e. the tracheostoma device and the tracheostoma device holder, must be kept high to ensure a repetitive and high frictional force. The latter may aggravate the manufacturing process.

Hence, an improved system of tracheostoma device and tracheostoma device holder would be advantageous, and in particular a tracheostoma device and tracheostoma device holder allowing for convenient application of the tracheostoma device holder with improved retaining and sealing effect between the tracheostoma device holder and the tracheostoma device, while simultaneously allowing for convenient removal of tracheostoma device from the tracheostoma device holder.

SUMMARY

Accordingly, the present invention preferably seeks to mitigate, alleviate or eliminate one or more of the above-identified deficiencies in the art and disadvantages singly or in any combination and solves at least the above mentioned problems by providing a tracheostoma device for cooperation with a tracheostoma device holder superimposed of a tracheostoma of a person, wherein said tracheostoma device comprises: a tubular body at the proximal end of the tracheostoma device, said tubular body comprising at least one inlet upon exhalation through the tracheostoma device, and said tubular body being adapted for cooperation with the tracheostoma device holder; a container at the distal end of the tracheostoma device, said container comprising at least one outlet upon exhalation through the tracheostoma device, said container being adapted for housing a heat and moisture exchanging foam; wherein the tubular body and the container have a hardness of less than and including 100 Shore A.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a tracheostoma device 100, for being held in a tracheostoma device holder 200 over the stoma of a person. A tracheostoma device 100 may in this context be a tracheostoma valve, HME, speech valve, etc., or combinations thereof.

Figure 1:
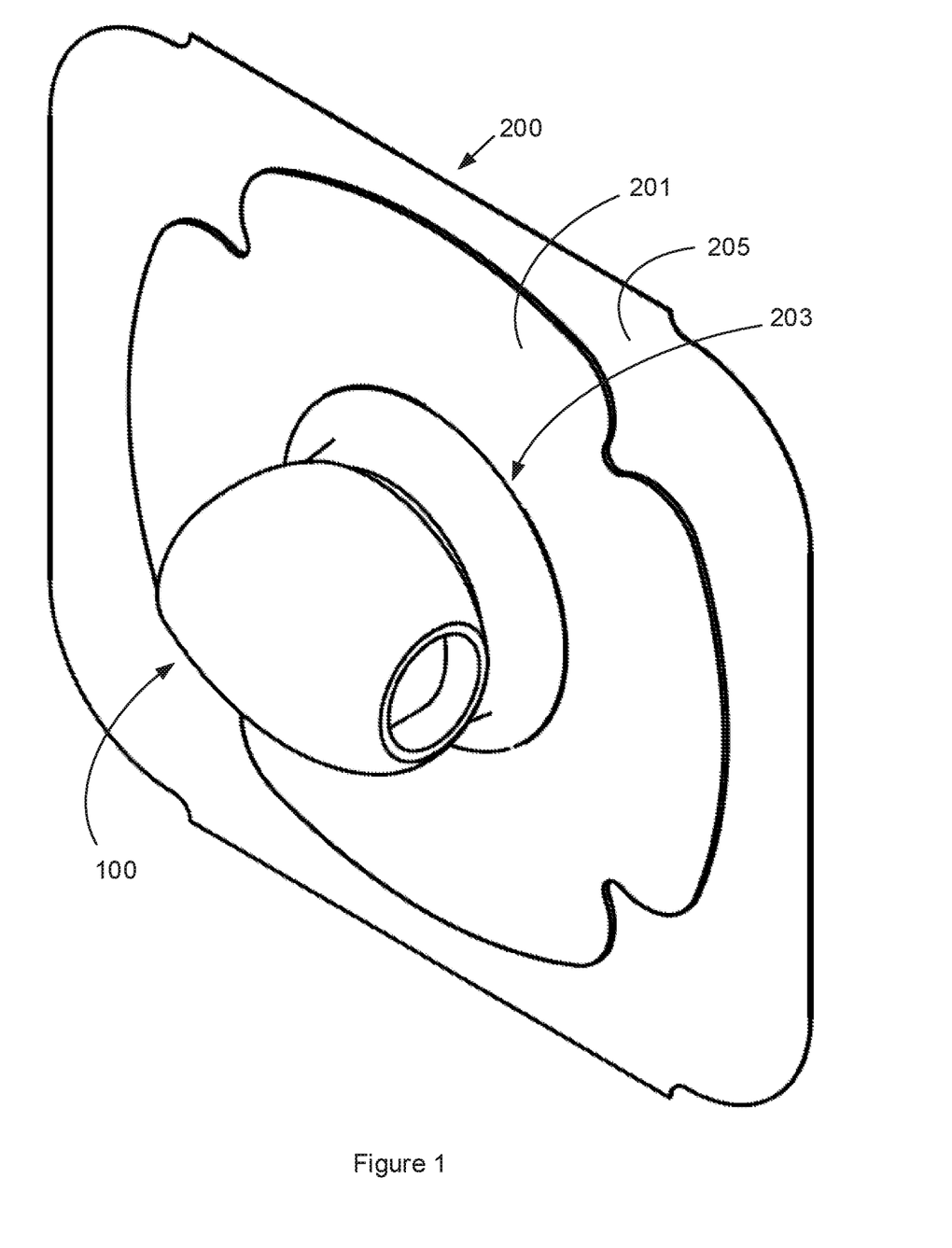
FIG. 1 is a perspective view of tracheostoma device in cooperation with a tracheostoma device holder according to an embodiment of the invention.
Figure 2A:
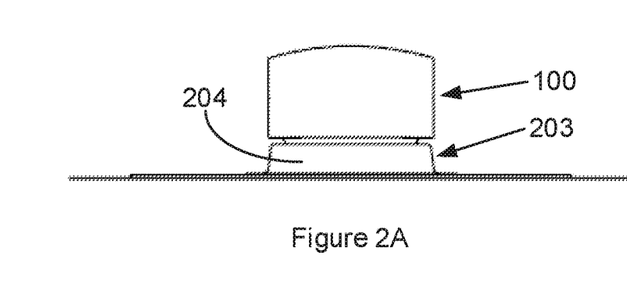
FIG. 2A is a front view of the tracheostoma device and tracheostoma device holder in FIG. 1.
Figure 2B:
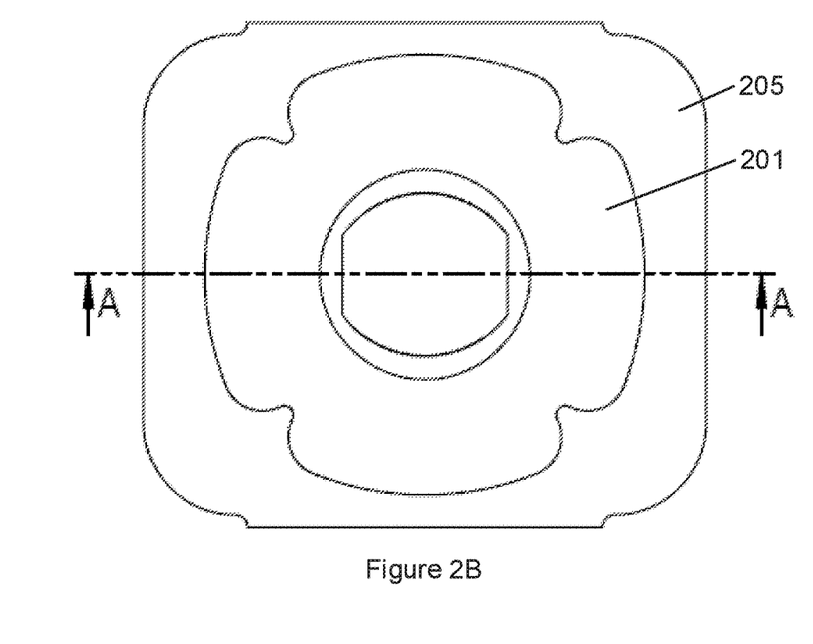
FIG. 2B is a top view of the tracheostoma device and tracheostoma device holder in FIG. 1.
Figure 2C:
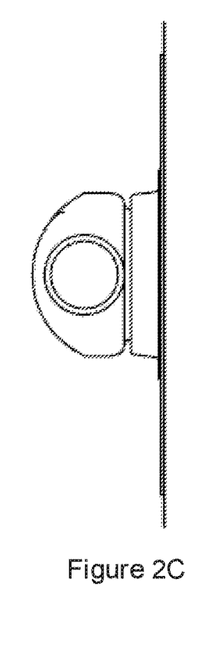
FIG. 2C is a side view of the tracheostoma device and tracheostoma device holder in FIG. 1.
Figure 2D:
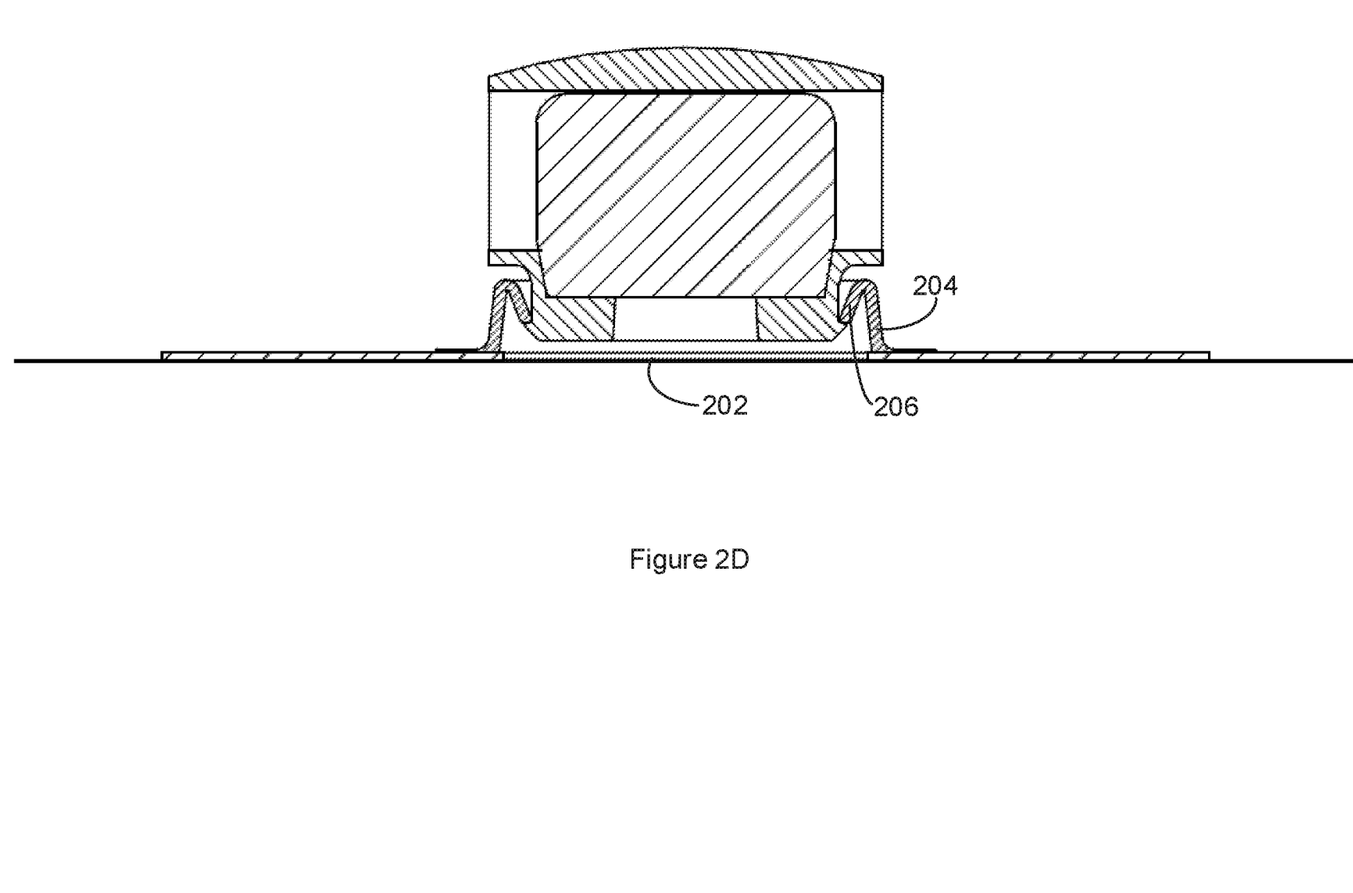
FIG. 2D is a front and cross-sectional view along A-A in FIG. 2B of the tracheostoma device and tracheostoma device holder in FIG. 1.
Figure 3:
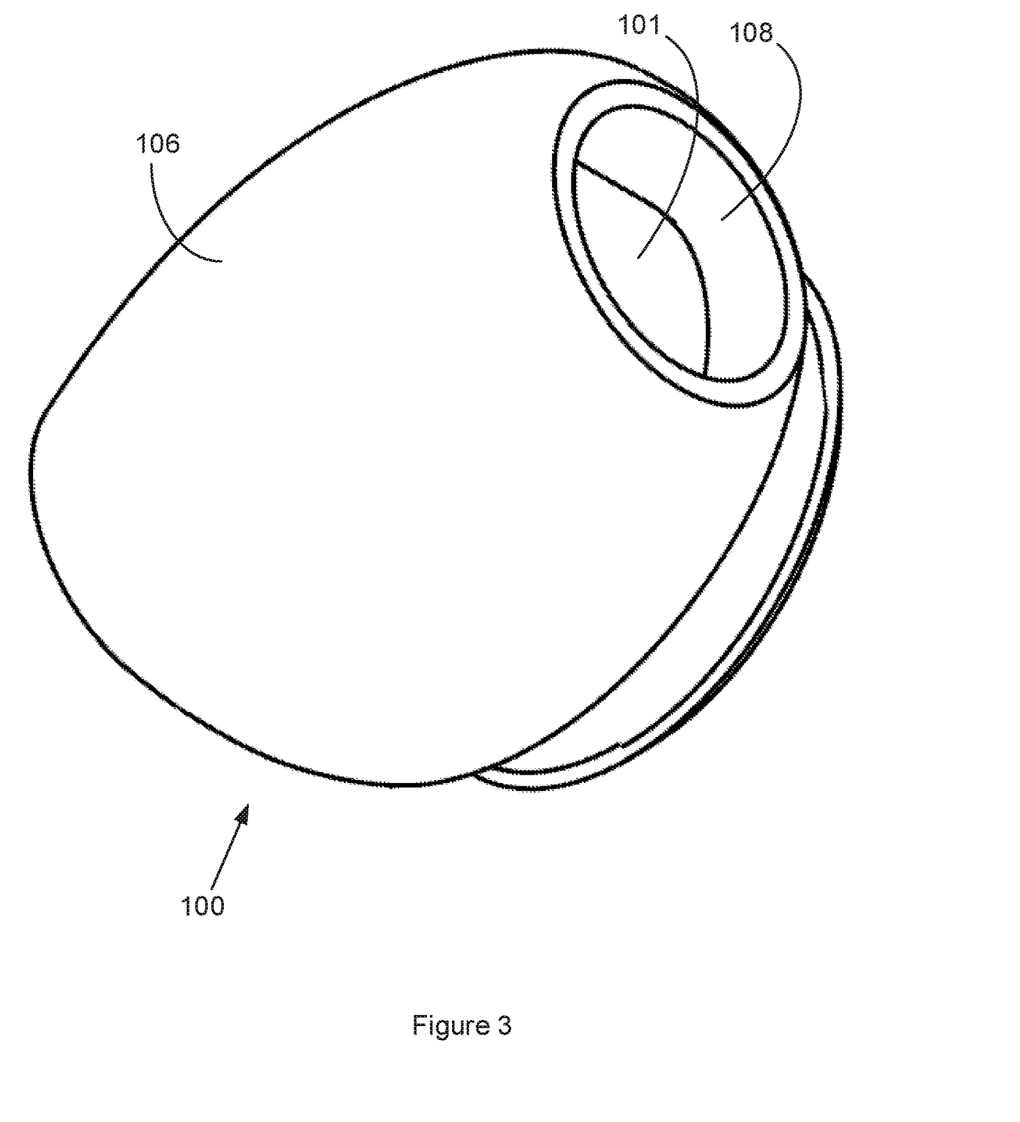
FIG. 3 is a perspective view of the tracheostoma device shown in FIG. 1.
Figure 4A:
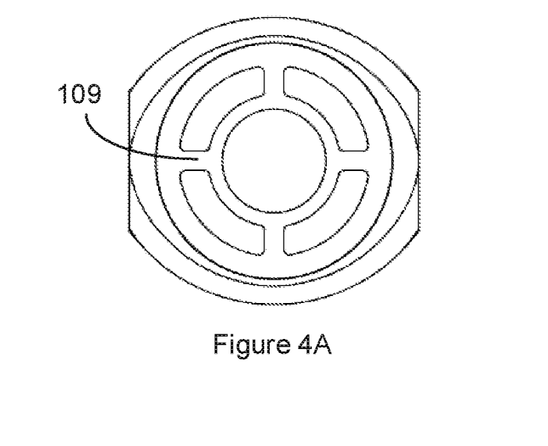
FIG. 4A is a bottom view of the tracheostoma device in FIG. 3.
Figure 4B:
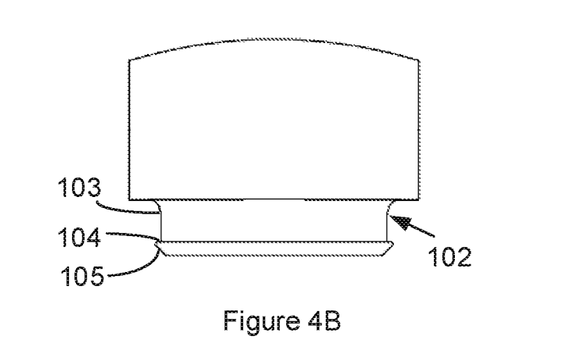
FIG. 4B is a front view of the tracheostoma device in FIG. 3.
Figure 4C:
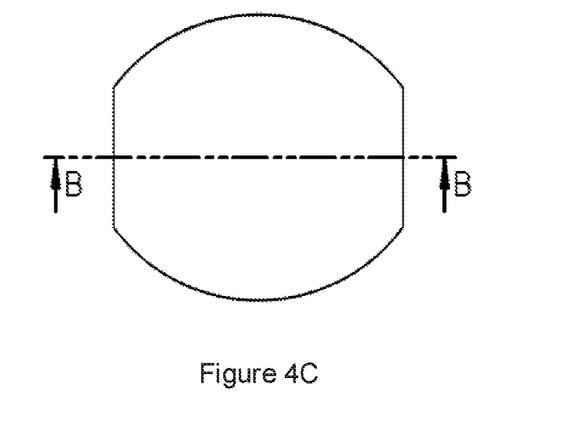
FIG. 4C is a top view of the tracheostoma device in FIG. 3.
Figure 4D:
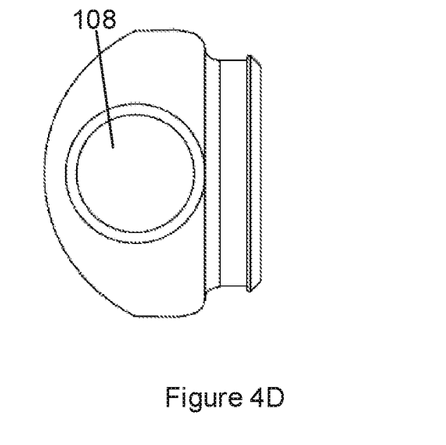
FIG. 4D is a side view of the tracheostoma device in FIG. 3.
Figure 4E:
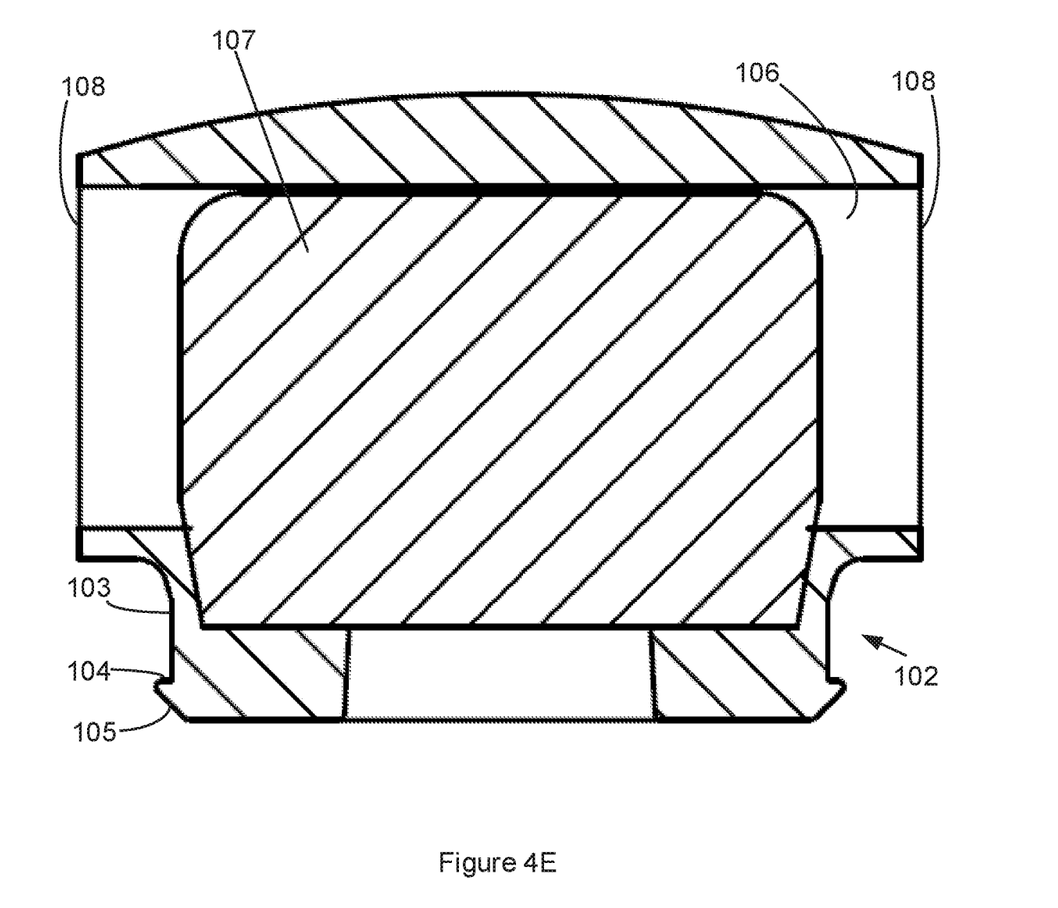
FIG. 4E is a front and cross-sectional view along B-B in FIG. 4C of the tracheostoma device in FIG. 3.

FIGS. 1 to 4 illustrate a tracheostoma device 100 for being held in a tracheostoma device holder 200, superimposed of a tracheostoma of a person, is disclosed. The tracheostoma device holder 200 comprises a skirt 201 for attachment over a tracheostoma via a skin adhesive proximal side thereof. The skirt 201 is preferably flexible. The skirt 201 is provided with a through hole 202. The tracheostoma device holder 200 also comprises a tubular tracheostoma device fitting 203. The tubular tracheostoma device fitting 203 is arranged circumferentially of the through hole 202. The tubular tracheostoma device fitting 203 extends distally from the distal side of the skirt 201. To this end, the tubular tracheostoma device fitting 203 comprises a sleeve 204, extending distally from the distal side of the skirt 201. The skirt 201 may comprise a proximal end sheet 205.

The tracheostoma device fitting 203 is made of a flexible and resilient material, such as rubber or silicone. In such configuration, the skirt 201 will extend laterally as a flange from the tubular tracheostoma device fitting 203, in relation to a central axis of the through hole 202. Similarly, the tubular tracheostoma device fitting 203 extends axially and distally from the skirt 201, in accordance with above.

The tracheostoma device fitting 203 also comprises a lip 206. The lip 206 is annular. The lip 206 extends proximally and centrally from the sleeve 204. The lip 206 may extend from the distal end zone of the sleeve 204, such as from the distal end of the sleeve 204. When the lip extends from the distal end of the sleeve 204, the manufacturing of the tracheostoma device holder 200 is facilitated and also the flexibility and length of the lip 206 may be adapted more freely to the relevant circumstances, i.e. the resistance force when placing the tracheostoma device 100 in the tracheostoma device fitting 203, the sealing force as a result of pressure difference between trachea and surroundings, and sealing force between the lip 206 and the tubular body 101 may be adapted after needs. To this end, the lip 206 extends proximally and centrally from the inner/central side wall of the sleeve 204. This inner/central side wall of the sleeve extends axially with the trough hole 202, defining the lumen of the tracheostoma device fitting 203. The proximally and centrally extending lip 206 will form a cavity laterally of the lip 206, i.e. in between the lip 206 and the sleeve 204. Because of this, the lip 206 will be able to flex outwardly/laterally upon pushing a tracheostoma device 100 into the thracheostoma device fitting 203.

The tracheostoma device 100 is provided with a tubular body 101 and a heel 102 at its proximal end zone, such as at the proximal end of the tracheostoma device 100. The heel 102 is continuously or discontinuously annular at the outer/lateral wall 103 of the tracheostoma device 100. The heel 102 is preferably provided with a distal ledge 104, extending perpendicularly to the central axis of the tracheostoma device 100 and/or the outer/lateral wall 103 of the tracheostoma device 100. The proximal end surface 105 of the heel 102 is preferably slanting inwardly/centrally. Distally of the tubular body 101, the tracheostoma device 100 is provided with a container 106, intended to house a heat and moisture exchanging foam 107 (HME). In this way, the container 106 in practice forms a HME housing. The container 106 may preferably be dome shaped, to decrease the number of edges that can be tangled up in clothing etc. The proximal end of the container 106 extends laterally beyond the tubular body 101, and preferably also laterally beyond the tracheostoma device fitting 203, the ensure enough space for housing a HME with enough heat and moisture exchanging capacity. The container 106 is provided with valve openings 108. The valve openings 108 may be arranged laterally, such that they may be occluded with a thumb and index finger grip. With this thumb and index finger grip, the openings 108 may be occluded to direct air flow into a speaking or speech creating direction. The two openings 108 with opening areas suitable to be closed with the thumb and index finger grip ensures enough breathing area to realize a low enough pressure drop over the tracheostoma device 100.

The proximal end surface 105 of the heel 102 may continuously push the lip 206 laterally/outwardly upon insertion of the tracheostoma device 100 into the tracheostoma device fitting 203, where after the lip 206 will snap centrally/inwardly distally of the ledge 104 of the heel 102. In this position, the lip 206 may seal against the outer/lateral wall 103 of the tracheostoma device 100—especially upon high pressure differences between the surroundings and the trachea. Due to this configuration, the retaining force and sealing effect will increase as the pressure difference between the surroundings and the trachea increases, since the distally directed force will push the lip 206 centrally/inwardly.

When removing/releasing the tracheostoma device 100 from the tracheostoma device holder 200, the tracheostoma device 100 may first be displaced laterally in relation to the tracheostoma device holder 200, until the heel 102 passes the lip 206 on one side of the arrangement of cooperation between the tracheostoma device 100 and the tracheostoma device holder 200. Here it is advantageous if the tubular body 101 is somewhat deformable, since then a deformation of the tracheostoma device 100 and its tubular body 101 may facilitate for the heel 102 to pass the lip 206. Since the tubular body 101 is placed in the device fitting 203 and being covered by the container 106, such that it is inaccessible when the tracheostoma device is fitted in the device fitting 203, it cannot be independently deformed if not the container 106 is deformable in the same way. For this reason it is advantageous if the tubular body 101 and the container 106 both are manufactured in a material having a hardness less than and including 100 Shore A (Shore ASTM D2240 type A—for softer plastics). Also, when the tubular body 101 and the container 106 is manufactured in plastics having a hardness of 100 Shore A (or below 100 Shore A) it is even possible to injection mold these parts as a monolithic item, since it is then possible to force off the product from the mold core, optionally through the use of blowing air into the interface between the mold core and the product.

At the proximal end of the tubular body 101 a grid structure 109 is arranged for retaining the HME in the cavity formed by the tubular body 101 and the container 106. The grid openings in the grid structure 109 form the inlet of air into the tracheostoma device upon exhalation and outlet upon inhalation, whilst the valve openings 108 forms the inlet of air upon inhalation and outlet upon exhalation. The distal end of the grid structure 109 is arranged proximally of the distal end of the tubular body 101. In this way the risk of occluding the tracheostoma device 100 via compressing the tracheostoma device in the distal/proximal direction may be decreased, while simultaneously allowing for additional space for housing the HME in the space enclosed by the tubular body 101 and the container 106. The grid structure 109 is preferably of a material having the same hardness as the tubular body 101 and/or the container 106, i.e. 100 Shore A or less, since the grid structure 109 preferably also is deformed in the same way as the tubular body 101 and/or the container 106 upon removal of the tracheostoma device 100 from the tracheostoma device holder 200, as described above.

When removing the tracheostoma device 100 through lateral movement and/or deformation, the heel 102 on the other side of the arrangement is in closer cooperation. Once the heel 102 passes the lip 206, the tracheostoma device 100 may be rotated upwards to be released from its cooperation with the tracheostoma device holder 200.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma device for cooperation with a tracheostoma device holder superimposed on a tracheostoma of a person, wherein said tracheostoma device comprises:
   a tubular body at a proximal end of the tracheostoma device, said tubular body comprising at least one inlet upon exhalation through the tracheostoma device, and said tubular body being adapted for cooperation with the tracheostoma device holder; and
   a container at a distal end of the tracheostoma device, said container comprising at least one outlet upon exhalation through the tracheostoma device, said container being adapted for housing a heat and moisture exchanging foam;
   wherein the tubular body and the container have a hardness of 100 Shore A or less;
   wherein the tubular body is monolithic with the container; and
   wherein the container extends laterally beyond the tubular body; and wherein the tubular body has a central axis and an outer/lateral wall, and a heel at a proximal end zone of the tubular body, and wherein the heel provides a releasable connection with the tracheostoma device holder.

2. The tracheostoma device according to claim 1, wherein the container comprises two valve openings arranged laterally, and configured to be occluded with a grip of a thumb and an index finger.

3. The tracheostoma device according to claim 1, wherein the heat and moisture exchanging foam is arranged in the container.

4. The tracheostoma device according to claim 1, wherein the container is dome shaped.

5. The tracheostoma device according to claim 1, wherein the heel is continuously or discontinuously annular at the outer/lateral wall.

6. The tracheostoma device according to claim 1, wherein the heel is provided with a distal ledge, extending perpendicularly to the central axis.

7. The tracheostoma device according to claim 1, wherein a proximal end surface of the heel is slanting inwardly/centrally.

8. The tracheostoma device according to claim 1, wherein a grid structure is arranged at a proximal end of the tubular body.

9. The tracheostoma device according to claim 8, wherein a distal end of the grid structure is arranged proximally of a distal end of the tubular body.

10. The tracheostoma device according to claim 8, wherein the grid structure is of a material having a hardness of 100 Shore A or less.

11. The tracheostoma device according to claim 8, wherein the grid structure is monolithic with a least one of the tubular body and the container.

12. A tracheostoma device for a tracheostoma device holder, comprising:
   a proximal end including a tubular body configured to form at least one inlet in response to exhalation through the tracheostoma device; and a distal end including a container configured to form at least one outlet in response to exhalation through the tracheostoma device, said container including a housing configured to receive a heat and moisture exchanging foam;

wherein the tubular body is monolithic with the container; and wherein the container extends laterally beyond the tubular body; and wherein the tubular body has a central axis and an outer/lateral wall, and a heel at a proximal end zone of the tubular body, and wherein the heel provides a releasable connection with the tracheostoma device holder.

13. The tracheostoma device according to claim 12, wherein the container includes at least two valve openings arranged laterally, and configured to be occluded with a grip of a thumb and an index finger.

14. The tracheostoma device according to claim 12, further comprising the heat and moisture exchanging foam arranged in the container.

15. The tracheostoma device according to claim 12, wherein the heel is provided with a distal ledge, extending perpendicularly to the central axis.

16. The tracheostoma device according to claim 15, wherein a proximal end surface of the heel slants inwardly from the distal ledge.

17. The tracheostoma device according to claim 12, wherein the proximal end includes a grid structure.

18. The tracheostoma device according to claim 17, wherein the grid structure includes a distal end configured to be arranged proximally of a distal end of the tubular body.

\* \* \* \* \*